United States Patent
Dekker et al.

(10) Patent No.: US 10,327,333 B2
(45) Date of Patent: Jun. 18, 2019

(54) ELECTRONIC CIRCUIT ARRANGEMENT AND METHOD OF MANUFACTURING THE SAME

(71) Applicant: KONINKLIJKE PHILIPS N.V., Eindhoven (NL)

(72) Inventors: Ronald Dekker, Valkenswaard (NL); Vincent Adrianus Henneken, Utrecht (NL); Marcel Mulder, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1323 days.

(21) Appl. No.: 14/374,635

(22) PCT Filed: Feb. 20, 2013

(86) PCT No.: PCT/IB2013/051370
§ 371 (c)(1),
(2) Date: Jul. 25, 2014

(87) PCT Pub. No.: WO2013/128341
PCT Pub. Date: Sep. 6, 2013

(65) Prior Publication Data
US 2014/0371744 A1    Dec. 18, 2014

Related U.S. Application Data

(60) Provisional application No. 61/605,265, filed on Mar. 1, 2012.

(51) Int. Cl.
*H05K 1/11*    (2006.01)
*A61B 18/00*    (2006.01)
(Continued)

(52) U.S. Cl.
CPC .......... *H05K 1/115* (2013.01); *A61B 1/0008* (2013.01); *A61B 1/051* (2013.01); *A61B 8/12* (2013.01);
(Continued)

(58) Field of Classification Search
CPC ........................ H05K 1/115; A61B 18/1492
See application file for complete search history.

(56) References Cited

U.S. PATENT DOCUMENTS 3,899,362 A    12/1975    Cline et al.
5,528,080 A    6/1996    Goldstein
(Continued)

FOREIGN PATENT DOCUMENTS

DE    2827640    10/1980
WO    2008143461 A2    11/2008

OTHER PUBLICATIONS

"A New Electromagnetic Actuator Using Through-Hold Plating of Nicket/Iron Permalloy" Sadler et al, Center for Microelectronic Sensors and MEMS, 1999.

*Primary Examiner* — Michael F Peffley
*Assistant Examiner* — Samantha M Good

(57) ABSTRACT

The present invention relates to an electronic circuit arrangement (10) comprising: a substrate (12) having a first surface (12a) and a second surface (12b), an electronic circuit, an electrical connection part (16) for providing an electrical connection to the electronic circuit and being arranged on the first surface (12a), and at least one electrical wire (18). The electrical wire (18) comprises at least one conductive core (20) and an isolation (22) surrounding the conductive core (20). An end portion (18a) of the electrical wire (18) is an isolation-free portion for allowing access to the conductive core (20), wherein the end portion (18a) of the electrical wire (18) is connected to the electrical connection part (16). At least one through-hole (24) extending from the first (Continued)

surface (12a) to the second surface (12b) is provided in the substrate (12), wherein the electrical wire (18) is arranged through the through-hole (24).

10 Claims, 14 Drawing Sheets

(51) Int. Cl.
    *A61B 1/00*     (2006.01)
    *H01L 21/768*     (2006.01)
    *H01L 23/48*     (2006.01)
    *H01L 23/00*     (2006.01)
    *A61B 1/05*     (2006.01)
    *A61B 8/12*     (2006.01)
    *A61B 18/14*     (2006.01)
    *A61N 1/36*     (2006.01)
    *H05K 1/18*     (2006.01)
    *H05K 3/00*     (2006.01)
    *H05K 3/32*     (2006.01)
    *H01L 29/06*     (2006.01)

(52) U.S. Cl.
    CPC ...... *A61B 18/1492* (2013.01); *A61N 1/36135* (2013.01); *H01L 21/76898* (2013.01); *H01L 23/481* (2013.01); *H01L 24/03* (2013.01); *H01L 24/05* (2013.01); *H01L 24/46* (2013.01); *H01L 24/48* (2013.01); *H01L 24/72* (2013.01); *H01L 24/85* (2013.01); *H05K 1/18* (2013.01); *H05K 3/0094* (2013.01); *H05K 3/32* (2013.01); *A61B 2018/00577* (2013.01); *A61B 2018/00714* (2013.01); *A61B 2018/00791* (2013.01); *H01L 29/0657* (2013.01); *H01L 2224/0401* (2013.01); *H01L 2224/04042* (2013.01); *H01L 2224/0557* (2013.01); *H01L 2224/05166* (2013.01); *H01L 2224/05555* (2013.01); *H01L 2224/05624* (2013.01); *H01L 2224/05644* (2013.01); *H01L 2224/13101* (2013.01); *H01L 2224/16145* (2013.01); *H01L 2224/45565* (2013.01); *H01L 2224/4824* (2013.01); *H01L 2224/4847* (2013.01); *H01L 2224/85205* (2013.01); *H01L 2224/85365* (2013.01); *H01L 2224/85801* (2013.01); *H01L 2224/85815* (2013.01); *H01L 2924/00014* (2013.01); *H01L 2924/10155* (2013.01); *H01L 2924/10253* (2013.01); *H01L 2924/12042* (2013.01); *H01L 2924/181* (2013.01); *Y10T 29/49169* (2015.01)

(56) References Cited

U.S. PATENT DOCUMENTS

| | | | |
|---|---|---|---|
| 5,777,391 A | 7/1998 | Nakamura et al. | |
| 7,364,461 B1* | 4/2008 | Back | H01R 9/0515 |
| | | | 439/329 |
| 2006/0231751 A1 | 10/2006 | Zuleta et al. | |
| 2007/0126091 A1 | 6/2007 | Wood et al. | |
| 2007/0246819 A1 | 10/2007 | Hembree et al. | |
| 2008/0283951 A1* | 11/2008 | Nabe | H01L 21/76898 |
| | | | 257/433 |

* cited by examiner

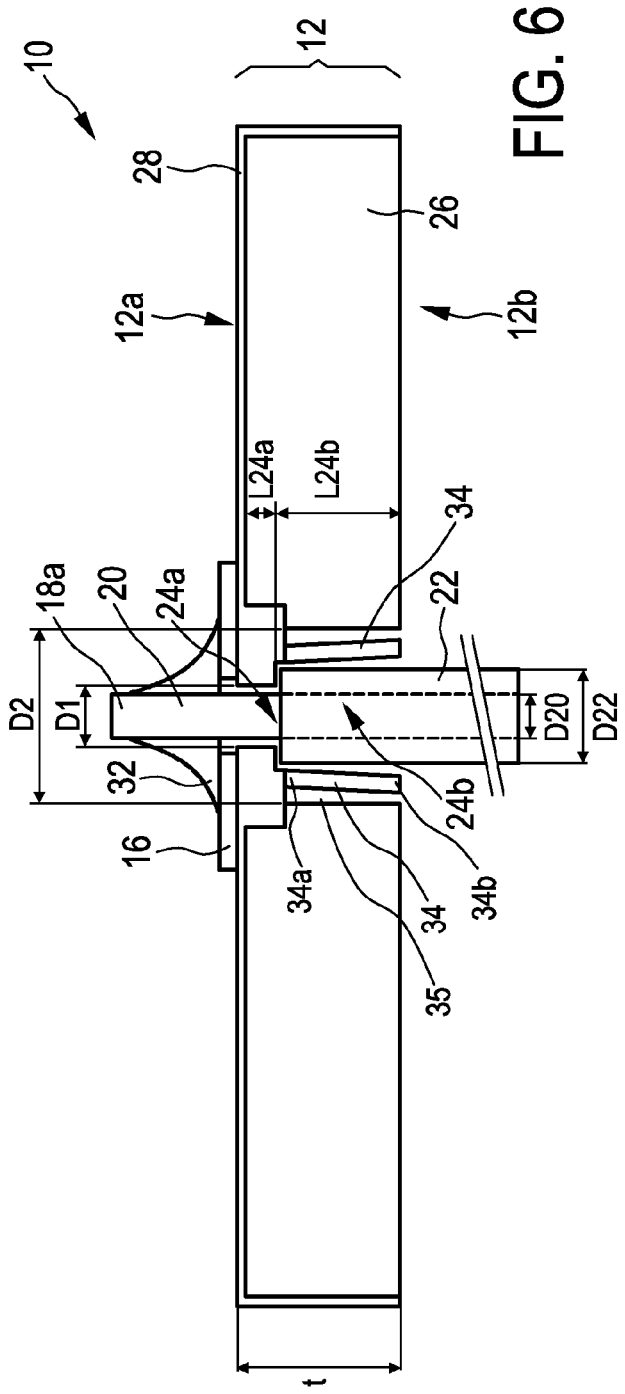
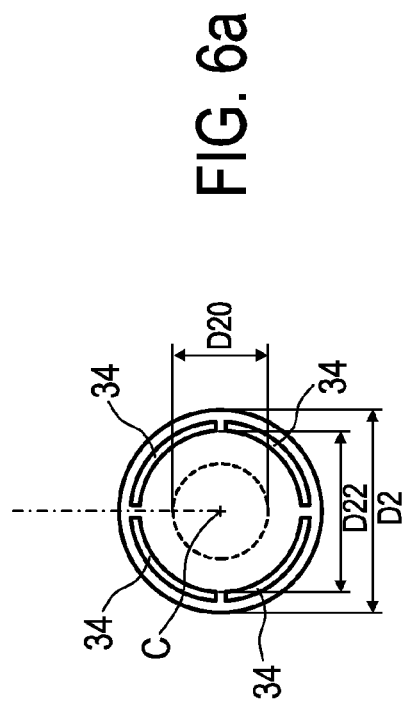

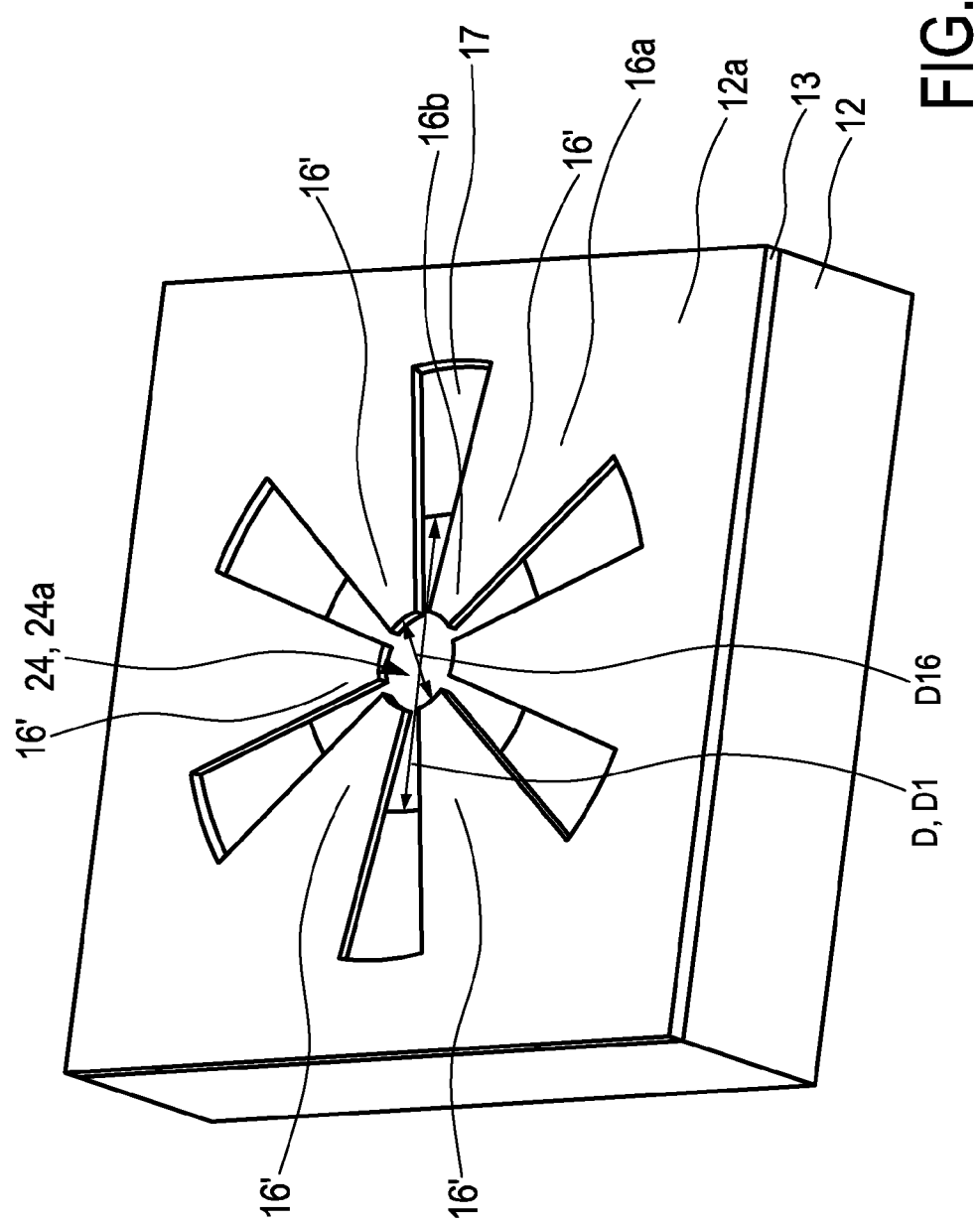

under 35 U.S.C. § 371 of International Application No. PCT/IB2013/051370, filed on Feb. 20, 2013, which claims the benefit of U.S. Provisional Application No. 61/605265 filed on Mar. 1, 2012. These applications are hereby incorporated by reference herein.

ELECTRONIC CIRCUIT ARRANGEMENT AND METHOD OF MANUFACTURING THE SAME

This application is a U.S. National Phase application under 35 U.S.C. § 371 of International Application No. PCT/IB2013/051370, filed on Feb. 20, 2013, which claims the benefit of U.S. Provisional Application No. 61/605265 filed on Mar. 1, 2012. These applications are hereby incorporated by reference herein.

FIELD OF THE INVENTION

The present invention relates to an electronic circuit arrangement (e.g. silicon chip) comprising a substrate (e.g. silicon wafer) and an electronic circuit. The present invention further relates to a method of manufacturing such electronic circuit arrangement. The present invention further relates to a sensor and/or actuator arrangement comprising such electrical circuit arrangement and at least one sensor and/or actuator (e.g. optical camera or ultrasound transducers). The present invention further relates to a medical instrument, in particular a minimal invasive medical instrument (e.g. a catheter or a catheter guide wire), with a proximal end and a distal end and comprising such sensor and/or actuator arrangement.

BACKGROUND OF THE INVENTION

There is a trend to integrate electronic functionality in the form of intelligent sensors and/or actuators in the tip of a minimal invasive medical instrument. These sensors and/or actuators can help the physician to guide the medical instrument through the body, or can allow for a more accurate diagnosis. Sensors and/or actuators, such as optical camera or ultrasound transducers, are well-known on the tip of endoscopes. However such electronic functionality is also envisioned for smaller medical instruments, in particular minimal invasive medical instruments, such as catheters or catheter guide wires.

These sensors and/or actuators are used in combination with electronic circuits. These electronic circuits need to be connected to electrical wires which run all the way from the distal end or tip of the minimal invasive instrument to the proximal end, where the instrument is for example connected to some readout device. Such an electrical wire can have a small diameter. The connection of the electrical wires to the electronic circuit arrangement (e.g. silicon chip), comprising a substrate and an electronic circuit is becoming an increasingly important problem. The electrical wires generally need to be connected to the electronic circuit arrangement (e.g. silicon chip) in a manual process, i.e. by hand. Such a manual assembly process is very difficult and time consuming. For example, the electrical wires can easily loosen. Also, the yield of the assembled electronic circuit arrangements can be very low (e.g. as low as 50%). As such, the assembly process of assembling and/or connecting the electrical wires to the electronic circuit constitute a significant, if not dominant, portion of the total cost of the medical instrument. Thus, the manufacturing of such electronic circuit arrangement or medical instrument is difficult and expensive.

SUMMARY OF THE INVENTION

It is an object of the present invention to provide an improved electronic circuit arrangement and method of manufacturing the same, in particular with easier and/or cheaper manufacturing. A further object to the present invention is to provide a corresponding sensor and/or actuator arrangement and a corresponding medical instrument.

In a first aspect of the present invention an electronic circuit arrangement is presented comprising a substrate having a first surface and a second surface, an electronic circuit, an electrical connection part for providing an electrical connection to the electronic circuit and being arranged on the first surface, and at least one electrical wire. The electrical wire comprises at least one conductive core and an isolation surrounding the conductive core, wherein an end portion of the electrical wire is an isolation-free portion for allowing access to the conductive core. The end portion of the electrical wire is connected to the electrical connection part. At least one through-hole extending from the first surface to the second surface is provided in the substrate, wherein the electrical wire is arranged through the through-hole.

In a further aspect of the present invention a sensor and/or actuator arrangement comprising the electrical circuit arrangement of the invention and at least one sensor and/or actuator is presented. The electrical circuit is configured to transmit electrical signals to the at least one actuator and/or receive electrical signals from the at least one sensor.

In a further aspect of the invention a medical instrument, in particular a minimal invasive medical instrument, having a proximal end and a distal end and comprising the sensor and/or actuator arrangement of the invention is presented. The sensor and/or actuator arrangement is arranged at the distal end of the medical device In a further aspect of the invention a method of manufacturing an electronic circuit arrangement comprising an electrical circuit is presented, the method comprising: providing a substrate having a first surface and a second surface, providing an electrical connection part for providing an electrical connection to the electronic circuit and being arranged on the first surface, providing in the substrate at least one through-hole extending from the first surface to the second surface, and arranging at least one electrical wire through the through-hole. The electrical wire comprises a conductive core and an isolation surrounding the conductive core, wherein an end portion of the electrical wire is an isolation-free portion for allowing access to the conductive core. The method further comprises connecting the end portion of the electrical wire to the electrical connection part.

The basic idea of the invention is to provide (e.g. to etch) at least one through-hole extending through the whole thickness of the substrate or wafer (in particular a silicon substrate or silicon wafer) and to arrange or insert the electrical wire through the through-hole. The isolation-free end portion of the electrical wire is connected to the electrical connection part for providing an electrical connection to the electronic circuit. The electronic circuit can be integrated in the substrate or arranged on the substrate, in particular on the first surface, or can be arranged on another (second) substrate. The electrical wire is arranged or inserted from the second surface (or backside). It does therefore not obstruct the electrical circuit which is for example arranged on the first surface (or frontside). The manufacturing or assembling of such electrical circuit arrangement is easy and/or cheap.

The electrical circuit arrangement is in particular a miniature electrical circuit arrangement. The electrical wire is in particular a miniature electrical wire. For example, the miniature electrical wire can have an outer diameter of 150

μm or less, in particular 100 μm or less, in particular 50 μm or less, in particular 30 μm or less. The outer diameter is generally the diameter of the conductive core plus twice the thickness of the isolation layer. For example, the isolation layer can have a thickness of 20 μm or less, in particular 10 μm or less, in particular between 5 and 10 μm. The invention is particularly useful in a sensor and/or actuator arrangement (e.g. electronic sensor chip). This sensor and/or actuator arrangement can for example be mounted or arranged at the distal end or tip of a medical instrument, in particular a minimal invasive medical instrument (e.g. a catheter or a catheter guide wire).

Preferred embodiments of the invention are defined in the dependent claims. It shall be understood that the claimed method has similar and/or identical preferred embodiments as the claimed electronic circuit arrangement and as defined in the dependent claims. Further, it shall be understood that the claimed sensor and/or actuator arrangement and the claimed medical instrument has similar and/or identical preferred embodiments as the claimed electronic circuit arrangement.

In one embodiment, a plurality of through-holes are provided in the substrate, wherein an electrical wire or conductive core is arranged through each through-hole. For example, the electrical wire can comprise a plurality (or strand) of conductive cores and a (single) isolation surrounding the plurality of conductive cores. This is also known as a "miniature flat cable". By providing each through-hole extending through the whole thickness of the substrate, the connection of the plurality (or strand) of conductive cores to the electronic circuit arrangement (e.g. silicon chip) can be reduced to one or two operations, which allows a significant reduction of cost. For example, the isolation of the miniature flat cable can be stripped in one operation (e.g. by laser ablation). For example, in case of soldering, the wires or cores can all be soldered in one operation (e.g. by solder dipping).

In another embodiment, the substrate comprises a conductive or semi-conductive main portion and an isolating layer covering at least part of the main portion. In this way a conventional semi-conductor substrate or wafer is used, which provides for a cheap manufacturing. The isolating layer can in particular cover the sidewalls of the through-hole. For example, part of the isolating layer can be used as an etch stop layer in the manufacturing process.

In a variant of this embodiment, the main portion is made of silicon. In this way the through-hole can be easily provided in the silicon using conventional methods, in particular by etching. Silicone is a very convenient substrate material because it is very simple to etch, in particular to etch a through-hole through it.

In a further embodiment, the end portion of the electrical wire is connected to the electrical connection part using a wedge bonding connection or a solder connection. This provides an easy way of providing the electrical connection between the electrical connection part and the electrical wire.

In a further embodiment, the through-hole comprises a first portion open to the first surface and having a first diameter and a second portion open to the second surface and having a second diameter bigger than the first diameter. In this way, the conductive core cannot easily break. The electrical wire with its isolation and isolation-free end portion perfectly fits in the through-hole.

In a variant of this embodiment, the first diameter is equal or bigger than a diameter of the conductive core and smaller than a diameter of the isolation. In this way, a rim is formed in between the first portion and the second portion. The isolation can be stopped or blocked by this rim, but not the isolation-free end portion. In this way, the conductive core can extend through the smaller first portion, but the rim between the larger second portion and the smaller first portion stops or blocks the isolation. Thus, the through-hole is fitted to the form and/or dimensions of the electrical wire. In this way stability of the electrical wire is provided. In particular, the through-hole can hold the electrical wire in place.

In a further embodiment, the isolating layer covers the first surface and comprises a thick portion surrounding the through-hole. The thick portion has a thickness which is at least a length of the first portion of the through-hole. The thick portion provides electrical isolation and mechanical strength, in particular during insertion of the electrical wire through the through-hole.

In a further embodiment, the electrical connection part comprises at least one cantilever spring contacting the end portion of the electrical wire. In this way, the electrical wire only needs to be inserted through the through-hole and no further operation is needed to form the electrical connection between the electrical connection part and the electrical wire. In particular, at least two cantilever springs at opposing sides of the electrical wire or end portion can be provided. A cantilever spring is in particular a spring having a first end and a second end, wherein only one end is fixed. The cantilever spring can in particular have a first end attached to the substrate and a second end contacting the end portion and bended in a direction facing away from the first surface. In particular, the cantilever spring can be made of a metal, more particularly a plurality of metal layers. The cantilever spring can in particular be a tension spring which is designed to operate with a tension load so that the spring stretches as the load is applied to it.

In a further embodiment, the substrate comprises at least one cantilever spring portion holding the electrical wire in place. In this way the electrical wire can be kept attached to the substrate. In particular, at least two cantilever spring portions at opposing sides of the electrical wire can be provided. In particular, the substrate can comprise a hole next to the through-hole so that the cantilever portion is formed in between the through-hole and the hole. A cantilever spring portion in particular has a first end and a second end, wherein only one end is fixed. The cantilever spring portion can in particular have a first end fixed or attached to the substrate and a second end standing free. The cantilever spring portion in particular contacts the isolation of the electrical wire. For example, the first end of the cantilever spring portion can be fixed to the substrate at a radius from the centre of the through-hole which is smaller than the radius of the isolation of the electrical wire. Further, the first end can be fixed to the substrate at a radius from the centre bigger than the radius of the electrical core, so that it does not obstruct the isolation-free end portion of the wire. The second end of the cantilever spring portion can in particular be bended in a direction facing away from the electrical wire (or a direction facing away from the centre of the through-hole). The cantilever spring portion can in particular be a tension spring portion, which is designed to operate with a tension load so that the spring portion stretches as the load is applied to it.

In a further embodiment, the at least one sensor and/or actuator is at least one device selected from the group comprising an optical camera, an ultrasound transducer, and an temperature, pressure and/or flow sensor. These sensors and/or actuators are particularly useful in connection with a medical instrument, in particular a minimal invasive medical instrument, such as a catheter or guide wire catheter.

In one embodiment of the method, providing in the substrate a through-hole comprises providing a plurality of through-holes in the substrate, wherein an electrical wire or conductive core is arranged through each through-hole.

In another embodiment of the method, providing a substrate comprises providing a conductive or semi-conductive main portion of the substrate, and the method comprises covering at least part of the main portion with an isolation layer.

In another embodiment of the method, connecting the end portion of the electrical wire to the electrical connection part comprises wedge bonding or soldering.

In another embodiment of the method, providing in the substrate at least one through-hole comprises providing a first portion of the through-hole which is open to the first surface and has a first diameter and providing a second portion of the through-hole which is open to the second surface and has a second diameter bigger than the first diameter. In particular, the first diameter can be equal or bigger than the diameter of the conductive core and smaller than the diameter of the isolation.

In a further embodiment of the method, covering at least part of the main portion with an isolation layer comprises covering the first surface with the isolation layer and providing a thick portion surrounding the through-hole. In particular, the thick portion can have a thickness which is at least a length of the first portion of the through-hole. The length of the first portion is in the direction of the thickness of the substrate or orthogonal to the substrate surfaces.

In a further embodiment of the method, providing an electrical connection part comprises providing at least one cantilever spring for contacting the end portion of the electrical wire. This can for example be performed using a sacrificial layer (or release layer). The cantilever spring can in particular have a first end attached to the substrate and a second end bendable in a direction facing away from the first surface.

In a further embodiment of the method, the method further comprises providing in the substrate at least one cantilever spring portion holding the electrical wire in place. Providing in the substrate the cantilever spring portion can for example be performed by etching into the substrate or main portion a cantilever spring-like structure. Such etching may be performed from the second surface of the substrate, from the first surface of the substrate, or a combination of both.

BRIEF DESCRIPTION OF THE DRAWINGS

These and other aspects of the invention will be apparent from and elucidated with reference to the embodiment(s) described hereinafter. In the following drawings

FIG. 6 shows a schematic cross-section of an electronic circuit arrangement according to a sixth embodiment;

FIG. 6a shows a schematic bottom view of part of the electronic circuit arrangement of FIG. 6;

FIG. 7 shows a perspective view of part of the electronic circuit arrangement of FIG. 5;

DETAILED DESCRIPTION OF THE INVENTION

Figure 1:
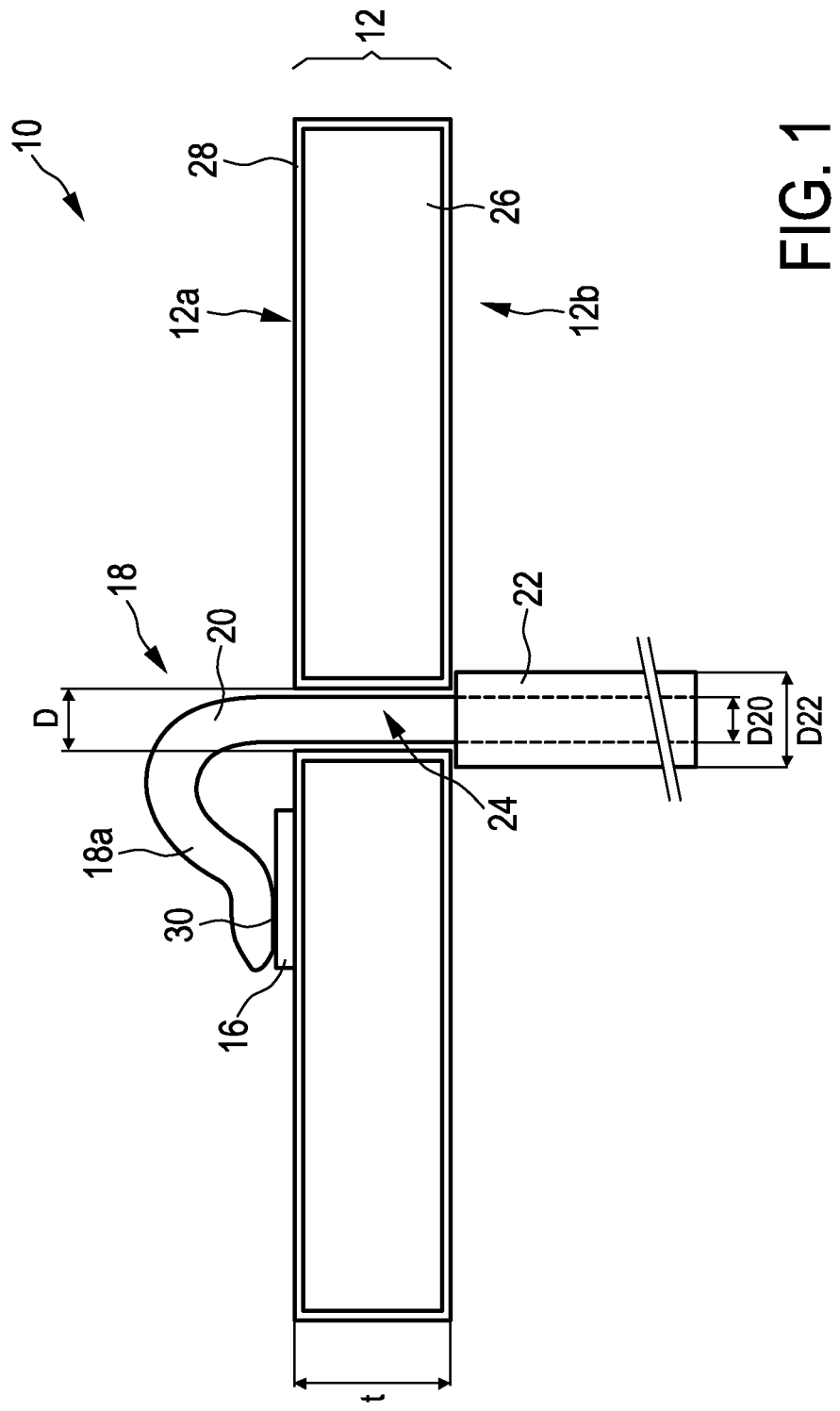
FIG. 1 shows a schematic cross-section of an electronic circuit arrangement according to a first embodiment.

FIGS. 1 to 6 each shows a schematic cross-section of an electronic circuit arrangement 10, in particular a miniature electronic circuit arrangement, according to a different embodiment. In each of FIGS. 1 to 6, the electronic circuit arrangement 10 comprises a (first) substrate 12 having a first surface (or frontside) 12a and a second surface (or backside) 12b, and an electronic circuit 14 (not shown in the Figures). The electronic circuit 14 can for example be integrated in the substrate or arranged on the substrate, in particular on the first surface 12a. Alternatively, the electronic circuit 14 can be arranged on another (second) substrate. For example, the second substrate with the electronic circuit 14 can then be mounted (e.g. by flip-chipping or solder bumping) on the first substrate.

The electronic circuit arrangement 10 further comprises an electrical connection part 16 (e.g. a pad or bondpad) for providing an electrical connection to the electronic circuit 12 and being arranged on the first surface 12a. The electronic circuit arrangement 10 further comprises at least one electrical wire 18. The electrical wire 18 comprises at least one conductive core 20 (having a diameter D20) and an isolation 22 (having a diameter D22) surrounding the conductive core 20. The isolation 22 is in the form of a ring-shaped isolation layer completely surrounding the circumference of the conductive core 20. An end portion 18a of the electrical wire 18 is an isolation-free portion for allowing access to the conductive core 20. The end portion 18a of the electrical wire 18 is connected to the electrical connection part 16. Furthermore, at least one through-hole 24 extending from the first surface 12a to the second surface 12b is provided in the substrate 12. The electrical wire 18 is arranged through the through-hole 24.

Thus, at least one through-hole 24 extending through the whole thickness t of the substrate 12 (or wafer) is provided (e.g. etched) in the substrate 12. The through-hole 24 in the shown embodiments is cylindrical with a diameter D. The electrical wire 18 is arranged or inserted from the second surface (or backside) 12b. Therefore, the electrical wire 18 does not obstruct the electrical circuit 14 which is for example arranged on the first surface (or frontside) 12a. The electrical wire 18 in the shown embodiments is in particular a miniature electrical wire, for example having an outer diameter D22 of 150 µm or less, in particular 100 µm or less, in particular 50 µm or less, in particular 30 µm or less. The outer diameter D22 of the electrical wire is the outer diameter D22 of the isolation. Thus, the outer diameter D22 is the diameter of the conductive core D20 plus twice the thickness of the isolation layer. For example, the isolation layer can have a thickness of 20 µm or less, in particular 10 µm or less, in particular between 5 and 10 µm. In a specific, but not-limiting example, the outer diameter D22 can be as small as 50 µm, including a 5 to 10 µm thick isolation layer.

In the shown embodiments, the substrate 12 comprises a conductive or semi-conductive main portion 26 and an isolating layer 28 covering at least part of the main portion 26. Preferably, the main portion 26 is made of silicon. However, it will be understood that any other suitable conductive or semi-conductive material can be used. The isolating layer 28 can for example be made of oxide, in particular silicon oxide. However, it will be understood that any other suitable isolating material can be used. In one example, the isolating layer 28 can be made of a dielectric (e.g. deposited by means of LPCVD, PEVCD or atomic layer deposition). In another example, the isolating layer can be made of polymer (e.g. parylene, which deposits very conformal and additionally is biocompatible). In an alternative embodiment, the substrate 12 can be entirely made of an isolating material (e.g. glass, quartz or a molded epoxy). The electrical connection part 16 (e.g. pad or bondpad) is made of a conductive material, in particular a metal (e.g. Aluminium or Gold). The conductive material or metal is bondable. For example, the electrical connection part 16 can be made of Gold, Aluminium, or an alloy thereof. For example, Titanium (not bondable) may be used as an adhesion layer underneath the Gold and/or Aluminium layer.

In a corresponding method for manufacturing an electronic circuit arrangement 10 comprising an electrical circuit 14, in particular according to any of the embodiments of FIGS. 1 to 6, the method first comprises a step of providing a substrate 12 having a first surface 12a and a second surface 12b. Then, the method comprises a step of providing an electrical connection part 16 for providing an electrical connection to the electronic circuit 12 and being arranged on the first surface 12a. Further, the method comprises a step of providing in the substrate 12 at least one through-hole 24 extending from the first surface 12a to the second surface 12b. The step of providing the through-hole 24 be performed before or after the step of providing the electrical connection part 16. Subsequently, the method comprises a step of arranging at least one electrical wire 18 through the through-hole 24, the electrical wire 18 comprising a conductive core 20 and an isolation 22 surrounding the conductive core 20, wherein an end portion 18a of the electrical wire 18 is an isolation-free portion for allowing access to the conductive core 20. Finally, the method comprises a step of connecting the end portion 18a of the electrical wire 18 to the electrical connection part 16. The step of arranging the wire 18 in the through-hole 24 and the step of connecting the end portion 18a to the electrical connection part 16 together form a so-called assembly step or assembly process.

In the shown embodiments, providing the substrate 12 comprises providing a conductive or semi-conductive main portion 26 (e.g. made of silicon) of the substrate 12, and the method comprises a further step of covering at least part of the main portion 26 with an isolation layer 28. In one example, the step of covering is performed after the through-hole 24 is provided. In this way, both the surface(s) 12a, 12b of the substrate and the sidewalls of the through-hole 24 can be covered in one step. In an alternative example, the step of covering is performed right after the substrate main portion 26 is provided. This can in particular be used in embodiments where the sidewalls of the through-hole 24 do not need to be covered with the isolating layer 28.

Figure 2:
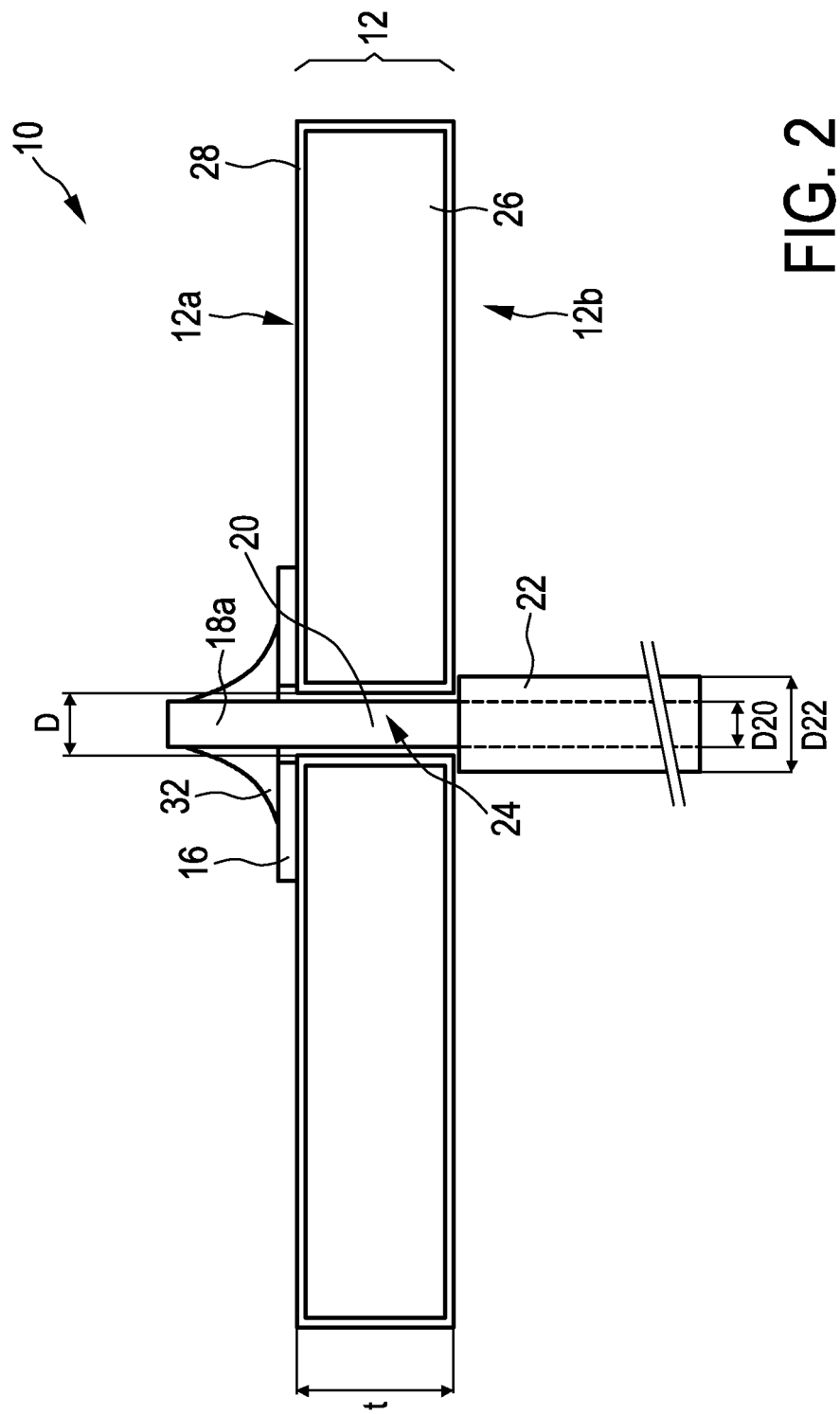
FIG. 2 shows a schematic cross-section of an electronic circuit arrangement according to a second embodiment.

FIG. 1 shows a schematic cross-section of an electronic circuit arrangement according to a first embodiment, and FIG. 2 shows a schematic cross-section of an electronic circuit arrangement according to a second embodiment. In the first embodiment of FIG. 1, the end portion 18a of the electrical wire 18 is connected to the electrical connection part 16 using a wedge bonding connection 30. In this embodiment, the isolation-free end portion 18a on the side of the first surface 12a bends towards the electrical connection part 16. In this embodiment, the electrical connection part 16 is only arranged on one side of the though-hole 24. In the alternative second embodiment of FIG. 2, the end portion 18a of the electrical wire 18 is connected to the electrical connection part 16 using a solder connection 32. In this embodiment, the isolation-free end portion 18a on the side of the first surface 12a is straight (in the direction orthogonal to the first surface) and the solder connection 32 is in the form of a solder joint (or solder bump) surrounding the end portion 18a. In this embodiment, the electrical connection part 16 has an annular or ring-shaped form surrounding the through-hole 24.

In general, the through-hole 24 is equal or bigger than the diameter D20 of the conductive core 20, so that the conductive core 20 or the end-portion 18a can reach the electrical connection part 16 on the first substrate surface 12a. In one example, the through-hole 24 can even be bigger than the diameter D22 of the isolation 22 (or outer diameter D22 of the wire), in particular along its entire depth or length or through the whole thickness t of the substrate 12. In this case, the depth or length to which the electrical wire needs to be inserted into the through-hole in order to reach the electrical connection part 16 would need to be determined, for example visually or by precision tooling.

In the embodiment of FIG. 1 or FIG. 2, the diameter D of the through-hole 24 is equal or bigger than the diameter D20 of the conductive core 20 and smaller than the diameter D22 of the isolation 22 (or outer diameter D22 of the wire). In this way, only the conductive core 20 extends through the trough-hole 24, but not the isolation 22. The isolation 22 ends at the point where the electrical wire 18 is inserted into the substrate (or wafer) 12 at the second surface 12b (or backside). Thus, assuming that the end-portion 18a is long enough to reach the electrical connection part 16, the electrical wire 18 or end-portion 18a only needs to be inserted into the through-hole 24 from the second surface 12b and the isolation 22 is stopped or blocked by the second surface 12b.

In the embodiment of FIG. 1 or FIG. 2, the isolating layer 28 covers the (entire) sidewalls of the through-hole 24. This is due to the fact that the conductive core 20 or isolation-free end-portion 16 is arranged through the entire through-hole 24. In this way, an electrical connection between the conductive core 20 and the conductive/semi-conductive main portion 26 of the substrate 12 can be prevented. In the embodiment of FIG. 1 or FIG. 2, the isolating layer also covers the first surface 12a and the second surface 12b.

Figure 9:
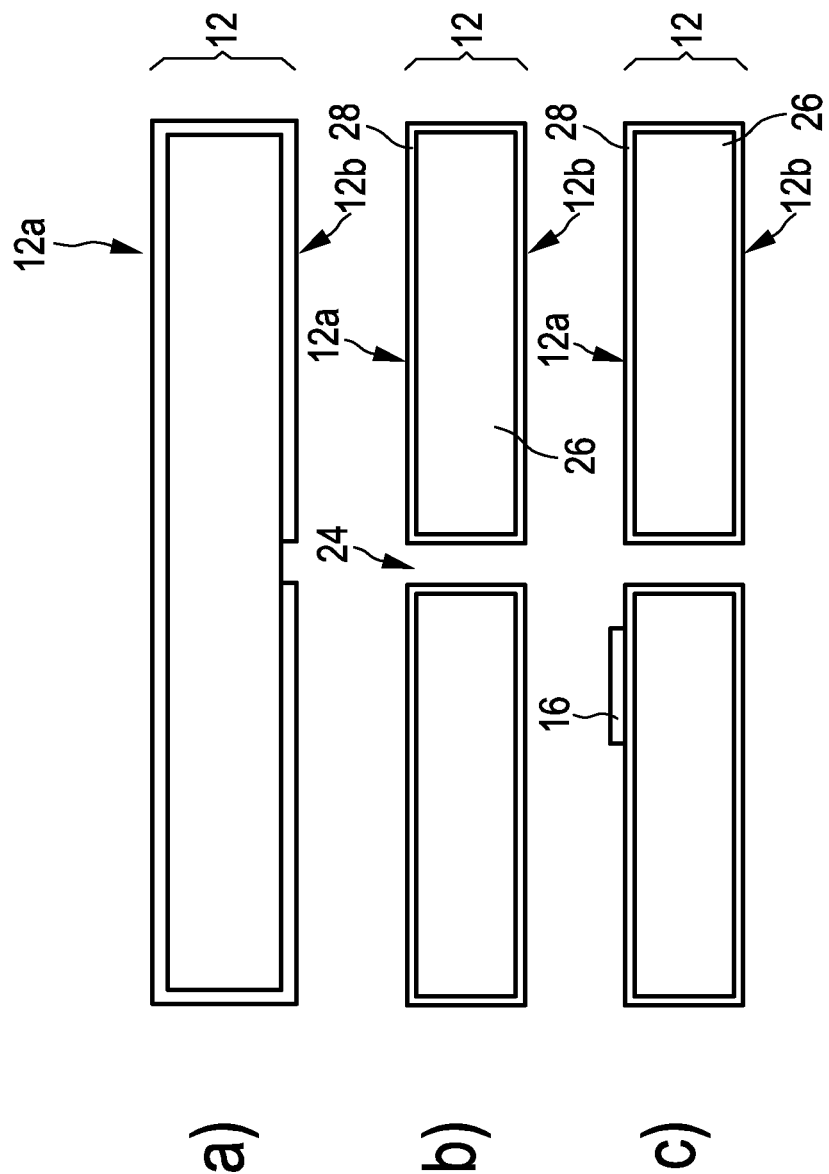
FIG. 9 shows part of an exemplary method of manufacturing of an electronic circuit arrangement according to the first embodiment of FIG. 1 or the second embodiment of FIG. 2.

FIG. 9 shows part of an exemplary method of manufacturing of an electronic circuit arrangement 10 according to the first embodiment of FIG. 1 or the second embodiment of FIG. 2. As shown in FIG. 9a, the method first comprises the step of providing the substrate 12 with the first surface 12a and the second surface 12b. In this example, providing the substrate 12 comprises providing the conductive or semi-conductive main portion 26 and covering at least part of the main portion 26 with the isolation layer 28. Then, referring to FIG. 9b, the method comprises the step of providing in the substrate 12 the through-hole 24 extending from the first surface 12a to the second surface 12b. For example, a removable support layer (e.g. made of polyimide) can be applied to the first substrate surface 12a before etching the through-hole 24, and removed after etching the through-hole 24. The support layer gives the substrate 12 mechanical support during etching (e.g. deep reactive-ion etching (DRIE)). Subsequently, as shown in FIG. 9c, the method comprises the step of providing the electrical connection part 16 for providing an electrical connection to the electronic circuit 12 and being arranged on the first surface 12a. Now, the electrical wire 16 can be assembled to the device/arrangement by first arranging the electrical wire 18 with the end portion 18a through the through-hole 24, and then connecting the end portion 18a of the electrical wire 18 to the electrical connection part 16. The connecting step is performed by wedge bonding for the embodiment of FIG. 1 and by soldering for the embodiment of FIG. 2. Thus, in the embodiment of FIG. 1 or FIG. 2, the step of connecting the end portion 18a to the electrical connection part 16 comprises wedge bonding (FIG. 1) or soldering (FIG. 2). This yields the electronic circuit arrangement as shown in FIG. 1 or FIG. 2. In the embodiment of FIG. 1 or FIG. 2, at the point where the electrical wire 18 is inserted into the substrate (or wafer) 12 at the second surface 12b (or backside), the conductive core 20 may be fragile and may even break. This problem may solved by an embodiment which will now be explained with reference to FIG. 3.

Figure 3:
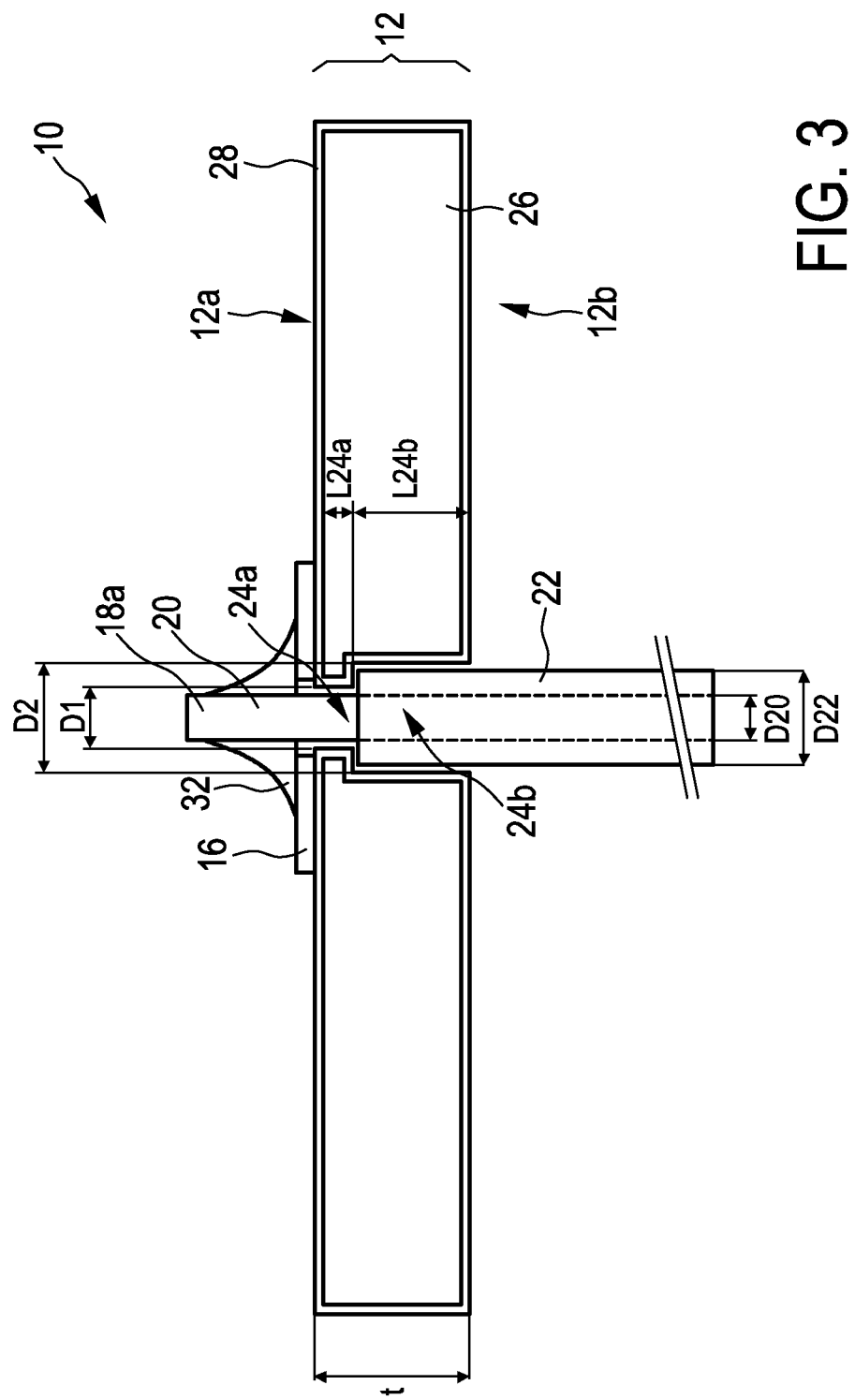
FIG. 3 shows a schematic cross-section of an electronic circuit arrangement according to a third embodiment.

FIG. 3 shows a schematic cross-section of an electronic circuit arrangement according to a third embodiment. In this third embodiment of FIG. 3, the through-hole 24 comprises a first portion 24a open to the first surface 12a and having a first diameter D1 and a second portion 24b open to the second surface 12b and having a second diameter D2 bigger than the first diameter D1. In a specific, but non-limiting example the second diameter is about twice the diameter of the first diameter D1 (i.e. double sized hole). The first diameter D1 is equal or bigger than the diameter D20 of the conductive core 20 and smaller than the diameter D22 of the isolation 22. In this way, a rim is formed in between the first portion 24a and the second portion 24b. The isolation 22 is stopped or blocked by this rim, but not the isolation-free end portion 16a. In this way, the conductive core 20 can extend through the smaller first portion 24a, but the rim between the larger second portion 24b and the smaller first portion 24b stops or blocks the isolation 22. Also, the second diameter D2 is equal or only slightly bigger than the diameter D22 of the isolation 22. Thus, the diameter D2 of the larger second portion 24b is selected such that it will just fit the isolation 22. In this way, the through-hole 24 is fitted to the form and/or dimensions of the electrical wire 18. In particular, the first portion 24a is fitted to the form and/or dimensions of the conductive core 20 or isolation-free end portion 18a, and the second portion is fitted to the form and/or dimensions of the isolation 22. The electrical wire 18 with its isolation 22 and isolation-free end portion 18a perfectly fits in the through-hole 24. Thus, the conductive core 20 cannot easily break. As can be seen in FIG. 3, the length L24b (in a direction orthogonal to the surfaces 12a, 12b) of the second portion 24b is bigger than the length L24a of the first portion 24a. However, it will be understood that the length 24a and the length 24b is fitted to the electrical wire 18 and its isolation-free end potion 18a, or vice versa. Thus, the length L24b can for example also be equal or smaller than the length L24a.

Figure 10:
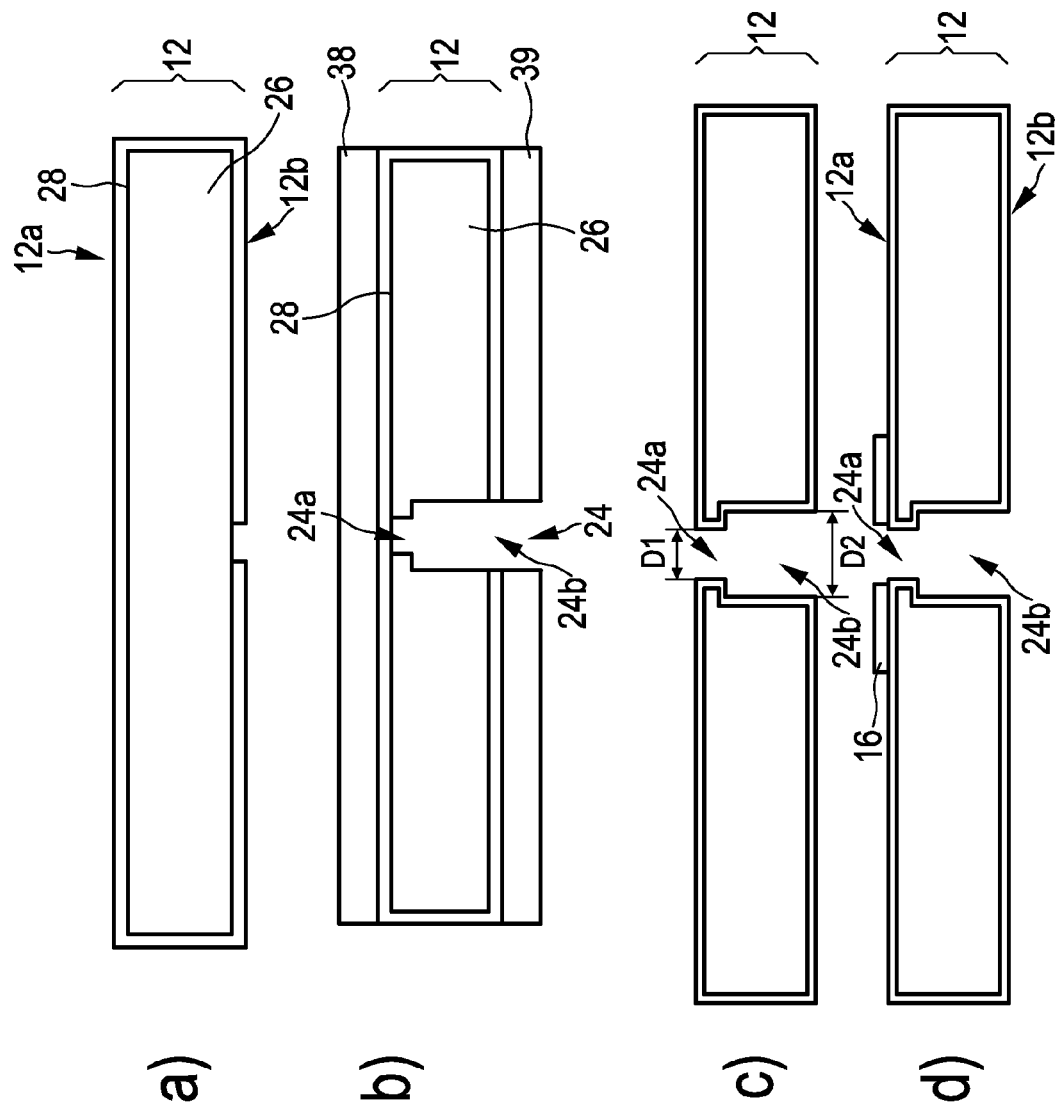
FIG. 10 shows part of an exemplary method of manufacturing of an electronic circuit arrangement according to the third embodiment of FIG. 3.

FIG. 10 shows part of an exemplary method of manufacturing of an electronic circuit arrangement 10 according to the third embodiment of FIG. 3. As shown in FIG. 10a, the method first comprises the step of providing the substrate 12 with the first surface 12a and the second surface 12b. Then, referring to FIG. 10b, the method comprises the step of providing in the substrate 12 the through-hole 24 extending from the first surface 12a to the second surface 12b. In this embodiment, providing the through-hole 24 comprises providing the first portion 24a of the through-hole 24 which is open to the first surface 12a and has the first diameter D1 and providing the second portion 24b of the through-hole 24 which is open to the second surface 12b and has the second diameter D2 bigger than the first diameter D1. This can for example be performed in a multiple step etch process (e.g. two step etch process). As shown in FIG. 10b, the larger second portion 24b of the through-hole 24 can be etched extending from the second surface 12b (or backside) and ending in the smaller first portion 24a. In the example of FIG. 10, part of the isolating layer 28 is used as an etch stop layer. In the example shown in FIG. 10, the step of providing the through-hole 24 comprises first applying a removable support layer 38 (e.g. made of polyimide) to the first substrate surface 12a for giving mechanical support of the substrate 12 during etching, then applying an etch stop mask 39 to the second substrate surface 12b, and afterwards etching (e.g. deep reactive-ion etching (DRIE)) the through-hole 24 from the second substrate surface 12b (e.g. multiple step etch process). Even though etching from the second substrate surface 12b is shown in FIG. 10, it will be understood that the through-hole 24 can also be etched from the first substrate surface 12a. Then, referring to FIG. 10c, the removable support layer 38 and the etch stop mask 39 are removed. Subsequently, as shown in FIG. 10d, the method comprises the step of providing the electrical connection part 16 for providing an electrical connection to the electronic circuit 12 and being arranged on the first surface 12a. Now, the electrical wire 16 can be assembled to the device/arrangement as explained above.

In the embodiment of FIG. 3, the isolating layer 28 covers the sidewalls of the first portion 24a and the second portion 24b, thus the entire through-hole 24. However, the isolating layer 28 could alternatively also only cover the sidewalls of the first portion 24a, as this is where an electrical connection between the conductive core 20 and the conductive/semi-conductive main portion 26 of the substrate 12 needs to be prevented. In the embodiment of FIG. 3, the isolating layer 28 also covers the first surface 12a and the second surface 12b.

As explained above, in each of the embodiments of FIG. 1, FIG. 2 and FIG. 3, after providing (e.g. etching) the through-holes, the sidewalls of the through-hole are isolated by means of an isolating layer 28 to prevent an electrical contact between the conductive core 20 and the conductive/semi-conductive main portion 26 of the substrate 12. In particular if the main portion 26 is made of silicon, which is (even if lightly doped) a conductor or more specifically a semi-conductor, an accidental electrical contact between the electrical wire 18 and the silicon main portion 26 might result in leakage currents which might disturb the proper operation of the electronic circuit or device. To prevent electrical contact between the conductive core 20 and the silicon main portion 26 is not always easy. Most techniques which result in a conformal deposition of an isolation layer 28 require a high processing temperature. For example, thermal oxidation is carried out at temperatures starting from about 900° C. Such high temperatures are likely to be incompatible with a prefabricated CMOS electrical circuit or CMOS device (e.g. sensor and/or actuator). The provision (e.g. etching) of the through-hole and the isolating layer therefore need to be performed before such prefabricated CMOS electrical circuit or CMOS device (e.g. sensor and/or actuator) are manufactured. However, the processing of a CMOS electrical circuit or CMOS device on a substrate (or wafer) with at least one through-hole in it is not easy. This problem may solved by an embodiment which will now be explained with reference to FIG. 4.

Figure 4:
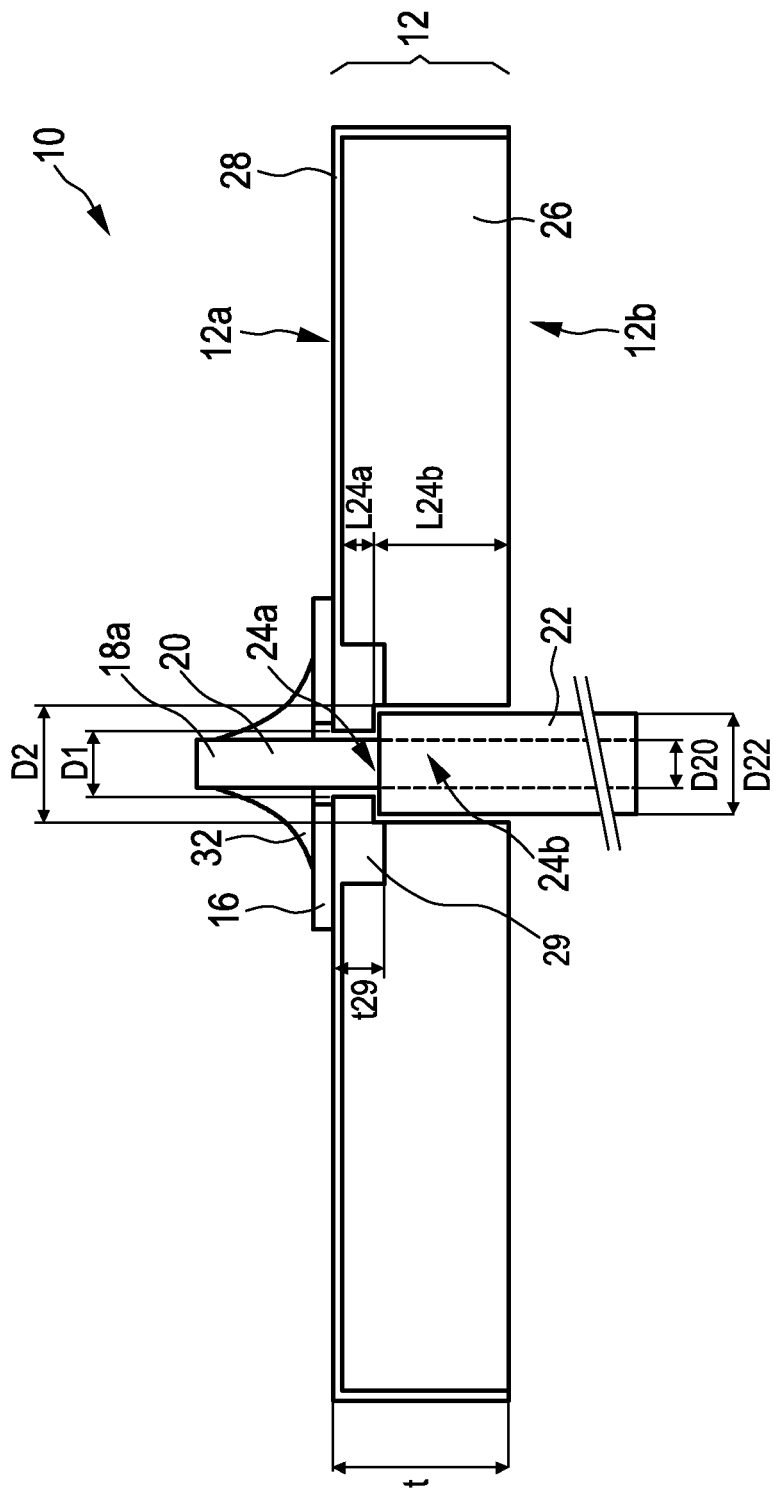
FIG. 4 shows a schematic cross-section of an electronic circuit arrangement according to a fourth embodiment.

FIG. 4 shows a schematic cross-section of an electronic circuit arrangement according to a fourth embodiment. In the embodiment of FIG. 4, the isolating layer 28 covers the first surface 12a and comprises a thick portion 29 surrounding the through-hole 24. A thickness is defined in a direction orthogonal to the substrate surfaces 12a, 12b. The thick portion 29 has a thickness t29 which is at least a length L24a of the first portion 24a of the through-hole 24. The length 24a of the first portion is in the direction of the thickness t of the substrate 12 or orthogonal to the surfaces 12a, 12b. The thick portion can in particular be made of an oxide (e.g. silicon oxide). Such a thick portion 29 does not only provide electrical isolation, but also mechanical strength during the insertion of the electrical wire 18. In this fourth embodiment shown in FIG. 4, the electrical core 20 can never come into contact with the (conductive) main portion 26 of the substrate, in particular the (conductive) sidewalls of the second portion 24b.

Figure 11:
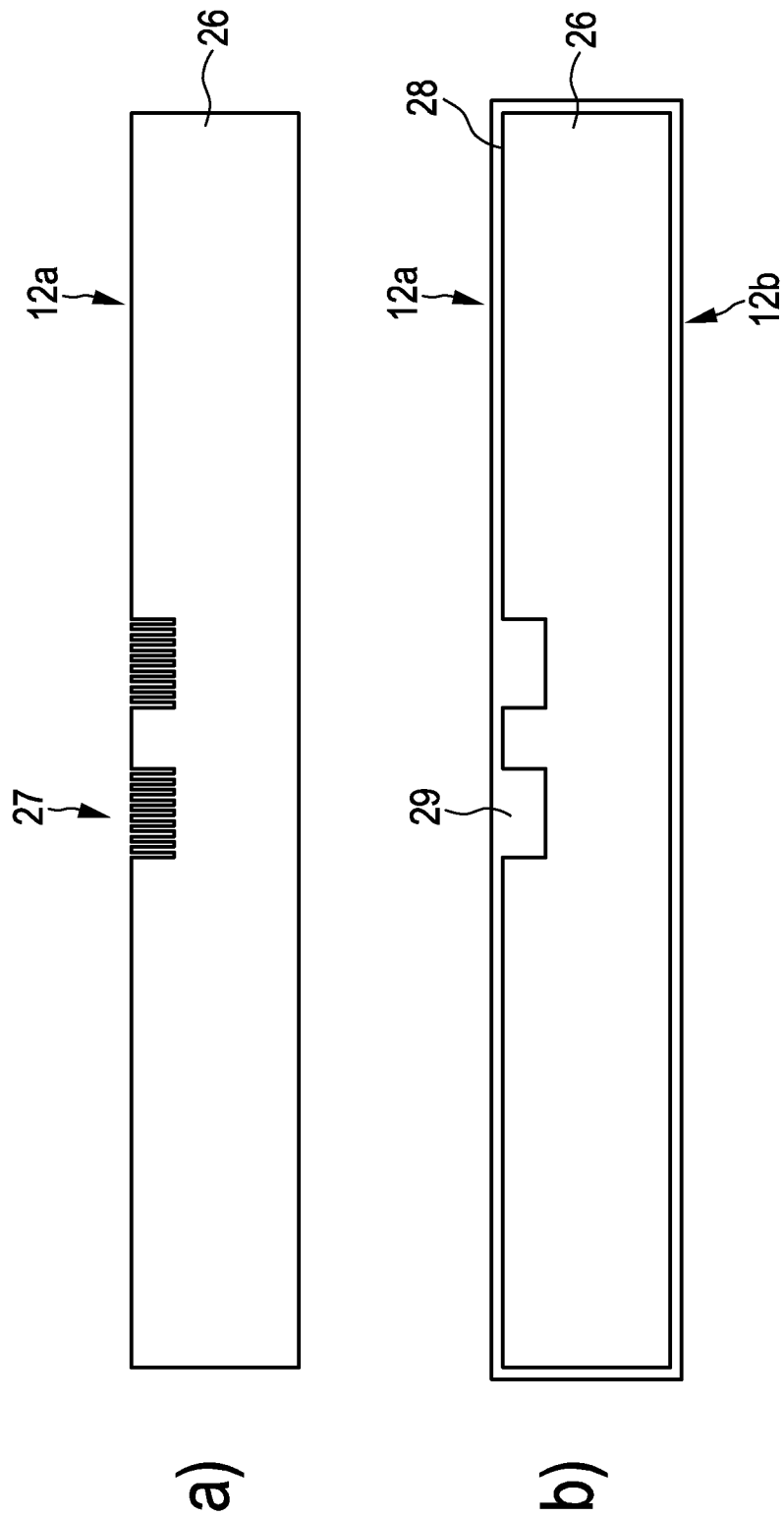
FIG. 11 shows part of an exemplary method of manufacturing of an electronic circuit arrangement according to the fourth embodiment of FIG. 4.

FIG. 11 shows part of an exemplary method of manufacturing of an electronic circuit arrangement according to the fourth embodiment of FIG. 4. In general, the method of manufacturing can be based on any of the methods described above, in particular as described in connection with FIG. 9 or FIG. 10. However, in this embodiment, the step of covering at least part of the main portion 26 of the substrate 12 with the isolation layer 28 comprises covering the first surface 12a with the isolation layer 28 and providing the thick portion 29 surrounding the through-hole 24. In this example of FIG. 11, as shown in FIG. 11a, the thick portion 29 is provided by providing, in particular etching, a plurality of adjacent (or fine grid of) trenches 27 from the first surface 12a into the substrate 12 or main portion 26. Subsequently the substrate 12 or main portion 26 in the region of the trenches 27 is oxidized to provide the thick portion 29. During the oxidation the substrate (e.g. silicone) expands so that a closed oxide layer is formed which is the thick (oxide portion) 29. This is a particular easy way of providing a thick (oxide) portion 29.

In particular, the first surface 12a can be covered with the isolation layer 28 before the CMOS electrical circuit or CMOS device (e.g. sensor and/or actuator) is manufactured or processed. If the method of FIG. 10 is combined with the method of FIG. 11 to form the thick oxide block 29, the step of providing the through-hole 24 in the substrate 12 can then comprise to end on this thick portion 29 of the isolating layer 28 during the provision, in particular etching, of the second portion 24b of the through-hole 24. In other words, the etching of the second portion 24b of the through-hole 24 stops at the thick (oxide) portion 29, but continues in the first portion 24a until finally the isolating or etch stop layer 28 on the first substrate surface 12a is reached. In this way, the first (smaller) portion 24a is defined by the frontside etch, allowing for much better defined features.

In the embodiment shown in FIG. 4, electrical connection between the isolation-free end portion 18a and the electrical connection part 16 is provided using a solder connection 32. However, it will be understood that any other suitable electrical connection can be used, in particular any of the other electrical connections disclosed herein.

Figure 5:
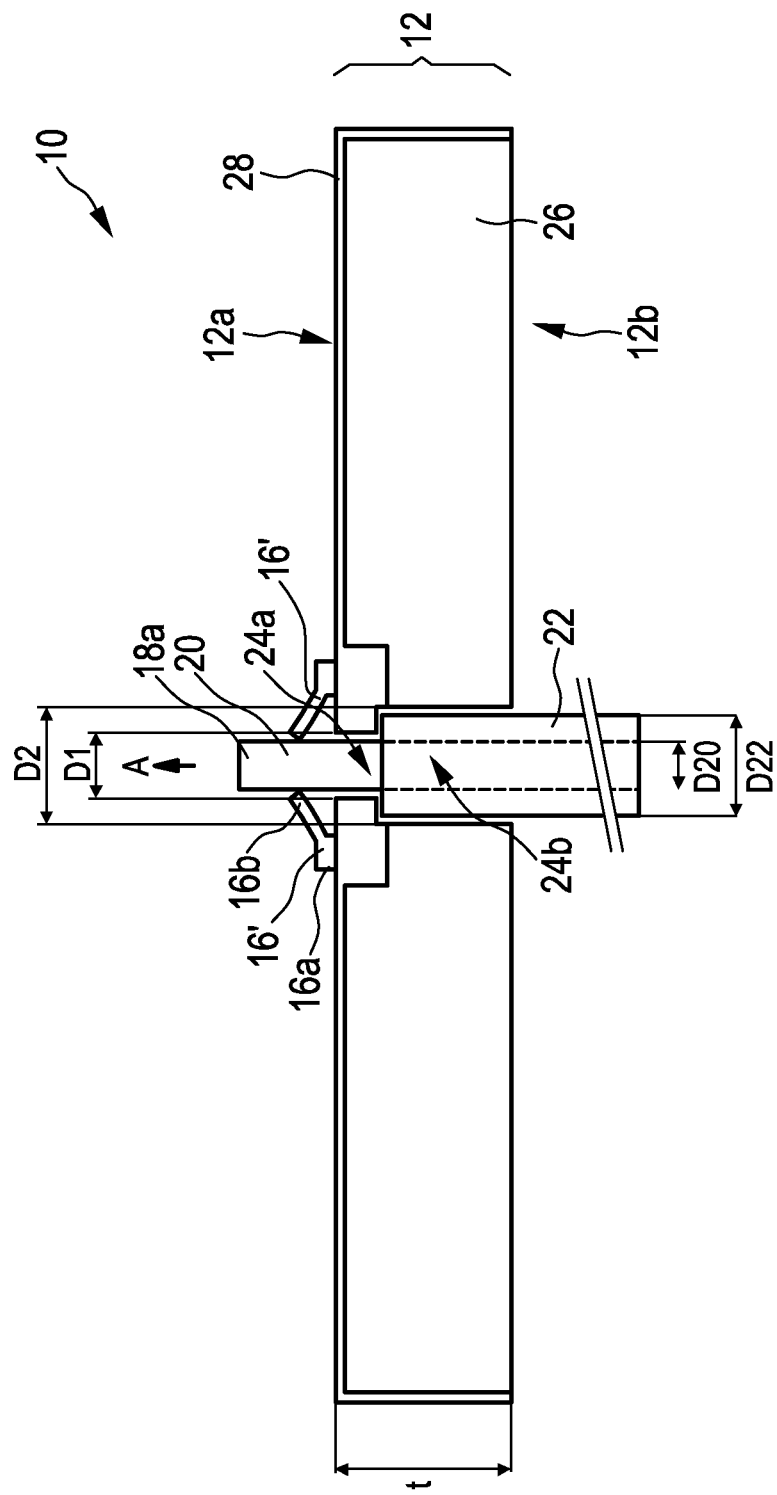
FIG. 5 shows a schematic cross-section of an electronic circuit arrangement according to a fifth embodiment.

Another electrical connection between the isolation-free end portion 18a and the electrical connection part 16 will now be described with reference to FIG. 5. FIG. 5 shows a schematic cross-section of an electronic circuit arrangement according to a fifth embodiment. In the fifth embodiment of FIG. 5, the electrical connection part 16 comprises at least one cantilever spring 16' contacting the end portion 18a of the electrical wire 18. In particular, at least two cantilever springs 16' at opposing sides of the electrical wire 18 or end portion 18a are provided. The cantilever spring 16' is a spring having a first end 16a and a second end 16b, wherein only one end is fixed. The cantilever spring 16' has a first end 16a attached to the substrate 12 and a second end 16b contacting the end portion 18a and bended in a direction facing away from the first surface 12a. The cantilever spring is in particular a tension spring, which is designed to operate with a tension load so that the spring stretches as the load is applied to it. The cantilever spring can only bend in one direction. After insertion of the electrical wire 18, the cantilever spring bends into that one direction, thereby trapping (or fastening) the electrical wire, but also providing electrical contact. The cantilever spring is also called a "Chinese finger trap". By using the described cantilever spring (or "Chinese finger trap"), after insertion of the electrical wire 18 no further operation (e.g. no wedge bonding or soldering) is needed. In this way an automatic connection is provided. The electrical wire only needs to be inserted through the through-hole 24. No further operation is needed to form the electrical connection between the electrical connection part 16 and the electrical wire 18.

The cantilever spring is a flat or non-coiled spring. In this embodiment, the cantilever spring is of a flat shaped piece of conductive material. However, it will be understood that the cantilever spring can have any other suitable form, for example a conical shaped piece of conductive material. In one example, the cantilever spring can be made of a metal, in particular a plurality of metal layers. The metal can for example be a stiff metal, in particular with a high Young's modulus (e.g. Tungsten). The cantilever spring can for example be realized by careful selection of metal layers and processing conditions. In this way, the cantilever spring can be realized in miniature on a substrate (e.g. made of silicon) using techniques such as deposition, lithography and etching. In an alternative example, the cantilever spring can be made of an isolating material coated with a conductive metal layer. The isolating material can in particular be a polymer. However, it will be understood that any other suitable isolating material can be used. In another alternative example, the cantilever spring can be made of a ceramic material coated with a conductive metal layer. The ceramic material can in particular be silicon, polysilicon, or silicon oxide. However, it will be understood that any other suitable ceramic material can be used.

In the embodiment shown in FIG. 5, the through-hole 24 comprises the first portion 24a and the second portion 24b as explained with reference to FIG. 3. However, it will be understood that any other suitable through-hole can be used, for example a through-hole having only one diameter, as in FIG. 1 or FIG. 2. Further, in the embodiment shown in FIG. 5, the isolating layer 28 comprises the thick portion 29 as explained with reference to FIG. 4. However, it will be understood that any other suitable isolating layer can be used.

It will be understood, that the electrical connection part 16 can comprise only one single cantilever spring 16'. In the same way, it will be understood, that the electrical connection part 16 can comprise a plurality of cantilevers springs 16', in particular at least two cantilevers springs 16'. FIG. 7 shows a perspective view of a first example of part of the electronic circuit arrangement of FIG. 5. As can be seen in FIG. 7, the electrical connection part 16 comprises a plurality of cantilever springs 16' each having a first end 16a attached to the substrate 12 and a second end 16b bendable in a direction facing away from the first surface 12a. In this example of FIG. 7, the cantilever springs 16' are made from a conductive layer 13 (e.g. made of metal) applied on the first substrate surface 12a. The cantilever springs 16' are arranged around a center hole of a diameter D16 in the conductive layer 13. The second end 16b of each cantilever spring 16' ends at the center hole of diameter D16. The diameter D16 of the center hole is here smaller than the diameter D of the through-hole 24 (or the first diameter D1 of the first portion 24a of the through-hole). Further, between each two cantilever springs 16' a recess 17 is formed in the conductive layer 13. In this way, the second end 16b of each cantilever spring 16' is cantilevered over the through-hole of diameter D or D1. Even though six cantilever springs are illustrated in FIG. 7, it will be understood that the electrical connection part 16 can comprise any suitable number of cantilever springs.

Figure 7A:
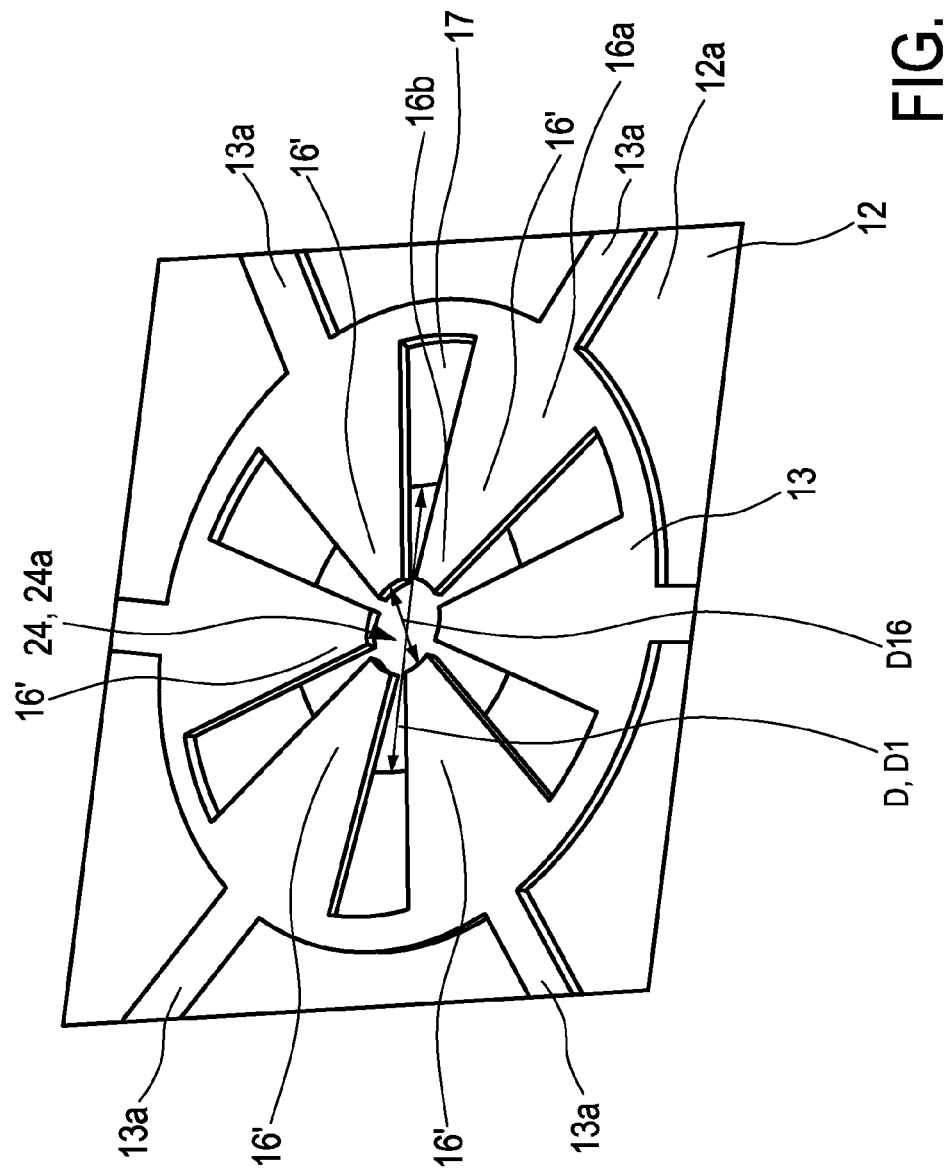
FIG. 7a shows a perspective view of a second example of part of the electronic circuit arrangement of FIG. 5.

FIG. 7a shows a perspective view of a second example of part of the electronic circuit arrangement of FIG. 5. As the second example of FIG. 7a is based on the first example of FIG. 7, the same explanations as for FIG. 7 also apply for FIG. 7a. In FIG. 7a the electrical connection part 16, or conductive layer 13, with the cantilever springs 16' has a circular shape with electrical connection arms 13a extending from the circular shape outwards. The electrical connection arms 13a then provide connection to the electrical circuit.

Figure 12:
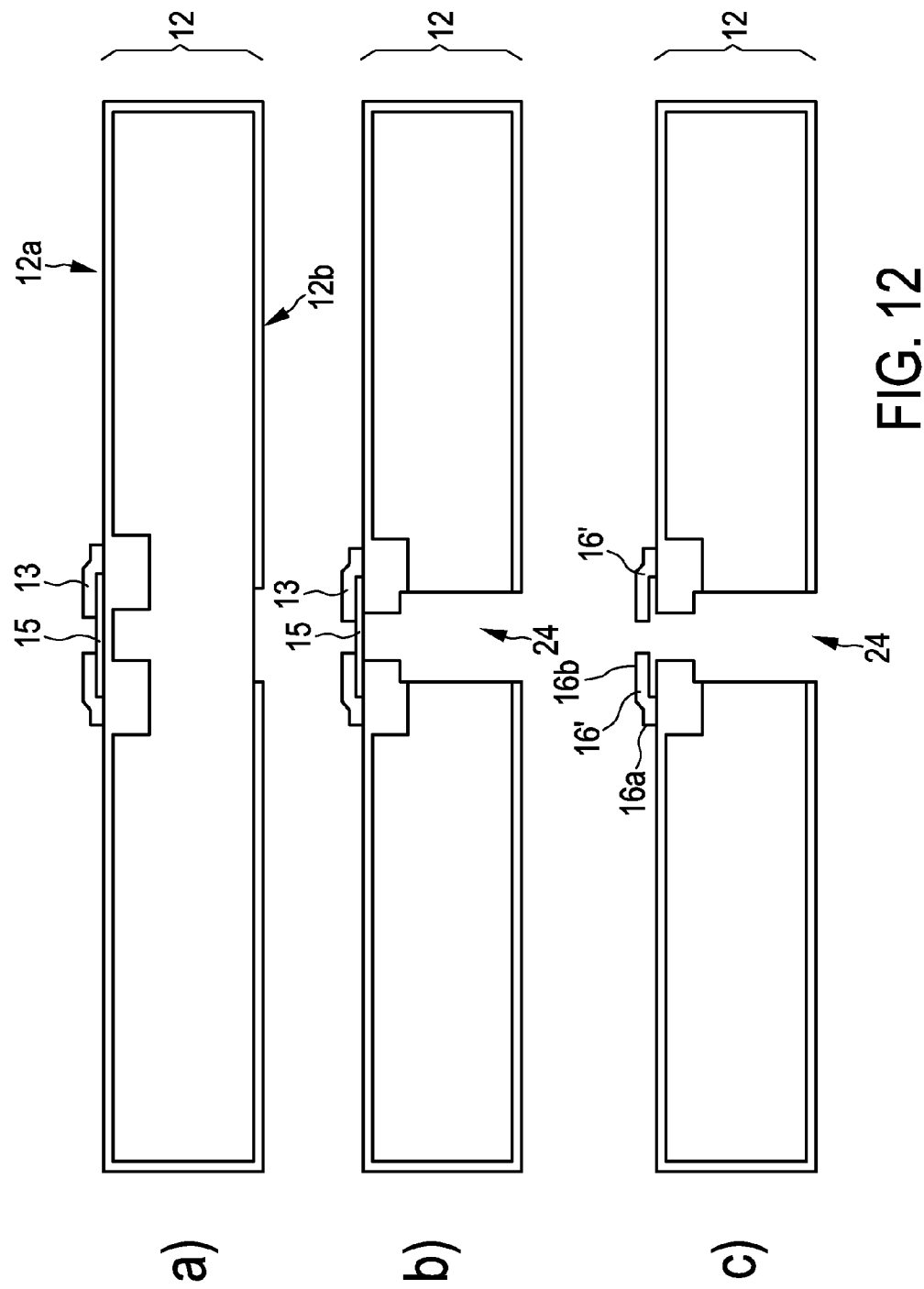
FIG. 12 shows part of an exemplary method of manufacturing of an electronic circuit arrangement according to the fifth embodiment of FIG. 5.

FIG. 12 shows part of an exemplary method of manufacturing of an electronic circuit arrangement according to the fifth embodiment of FIG. 5. In general, the method of manufacturing can be based on any of the methods described above, in particular in connection with FIG. 9, FIG. 10 or FIG. 11. However, in this embodiment, providing the electrical connection 16 part comprises providing the at least one cantilever spring 16' for contacting the end portion 18a of the electrical wire 18 (e.g. using a sacrificial or release layer 15). In the example of FIG. 12, this is performed by first providing a sacrificial layer 15 or release layer (e.g. made of Aluminium) on the first substrate surface 12a, then applying a conductive layer 13 (e.g. made of metal) completely covering the sacrificial layer 15, and providing a centre hole in the sacrificial layer 15 (e.g. by patterning). The sacrificial layer 15 can be initially patterned to provide a small pad as the sacrificial layer. For example, by varying the distance by which the sacrificial layer 15 protrudes in between the metal layer 13 and the substrate 12, the mechanical properties of the cantilever spring 16' can be adjusted. Then, referring to FIG. 12b, the step of providing the through-hole 24 is performed as explained above (e.g. using a removable support layer), in particular by etching the through-hole 24 centred around the centre hole of the conductive layer 13. Subsequently, the sacrificial layer 15 is removed (e.g. by etching, in particular wet etching). In this way, the cantilever spring 16' is formed. The first end 16a of the of the cantilever spring 16' is attached to the substrate 12 and the second end 16b of the cantilever spring 16' is cantilevered over the through-hole 24.

FIG. 6 shows a schematic cross-section of an electronic circuit arrangement according to a sixth embodiment, and FIG. 6a shows a schematic bottom view of part of the electronic circuit arrangement of FIG. 6. In the sixth embodiment of FIG. 6, the substrate 12 comprises at least one cantilever spring portion 34 holding the electrical wire 18 in place. In particular, at least two cantilever spring portions 34 at opposing sides of the electrical wire 18 are provided. The cantilever spring portion 34 has a first end 34a and a second end 34b, wherein only one end is fixed. In particular, the substrate comprises a hole 35 next to the through hole 24 so that the cantilever portion 34 is formed in between the through-hole 24 and the hole 35. The cantilever spring portion 34 has a first end 34a fixed or attached to the substrate 12 (here the thick portion 29 of the isolating layer 28) and a second end 34b standing free. The cantilever spring portion 34 contacts the isolation of the electrical wire 18. As can be seen in FIG. 6 and FIG. 6a, the first end 34a is fixed to the substrate 12 at a radius from the centre C of the through-hole 34 which is smaller (or at most equal) to the radius D22/2 of the isolation 22 of the electrical wire 18. Further, the first end 34a is fixed to the substrate 12 at a radius from the centre C bigger than the radius D20/2 of the electrical core 20, so that it does not obstruct the isolation-free end portion 18a of the wire. The second end 34b of the cantilever spring portion 34 is bended in a direction facing away from the electrical wire 18 (or a direction facing away from the centre C of the through-hole 24). The cantilever spring portion 34 is in particular a tension spring portion, which is designed to operate with a tension load so that the spring portion stretches as the load is applied to it. The cantilever spring portion 34 can only bend in one direction. After insertion of the electrical wire 18, the cantilever spring portion 34 bends into that one direction, thereby trapping (or fastening) the electrical wire 18. In this way the electrical wire can be kept attached to the substrate.

It will be understood, that the substrate 12 can also comprise a plurality of cantilever spring portions 34. In the bottom view shown in FIG. 6a, a plurality of cantilevers spring portions 34 are shown. Even though four cantilever spring portions 34 are illustrated in FIG. 6a, it will be understood that the substrate 12 can comprise any suitable number of cantilever springs portions 34. In this example, the cantilever portions 34 are arranged in a circle surrounding the electrical wire 18.

Figure 13:
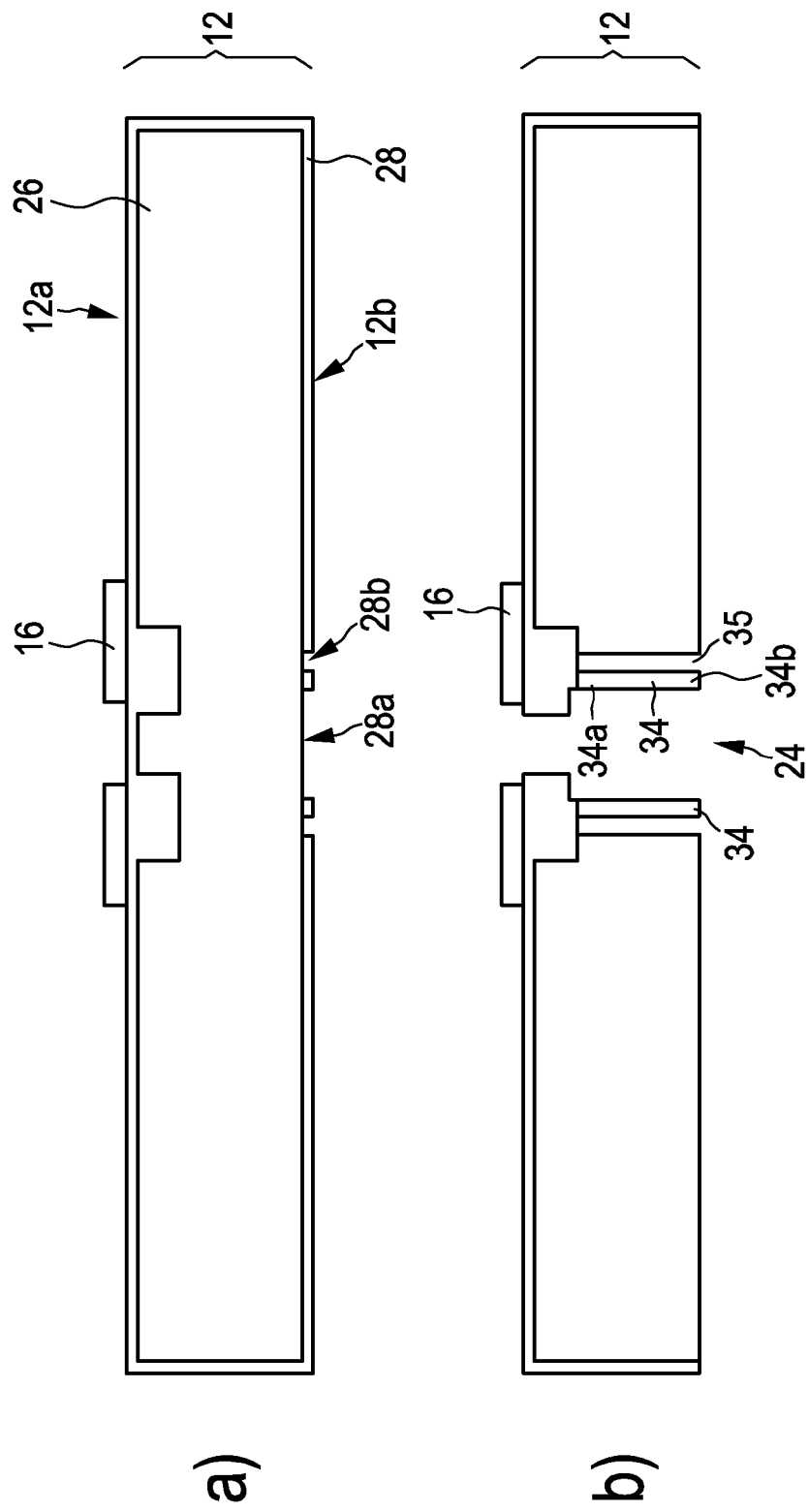
FIG. 13 shows part of an exemplary method of manufacturing of an electronic circuit arrangement according to the sixth embodiment of FIG. 6.

FIG. 13 shows part of an exemplary method of manufacturing of an electronic circuit arrangement according to the sixth embodiment of FIG. 6. In general, the method of manufacturing can be based on any of the methods described above, in particular in connection with FIG. 9, FIG. 10 or FIG. 11. However, in this embodiment, the method further comprises a step of providing in the substrate 12 the at least one cantilever spring portion 34 holding the electrical wire 18 in place. As shown in FIG. 13, providing the cantilever spring portion 34 can be performed by etching into the substrate 12 or main portion 26 (e.g. silicon) a cantilever spring-like structure. In the specific example of FIG. 13, first a hole 28a for etching of the through-hole 24 is provided in the isolating or etch stop layer 28 on the second substrate surface 12b, and next to the hole 28a there is provided a hole 28b for etching the cantilever spring portion 34, as shown in FIG. 13a. Then, referring to FIG. 13b, the step of providing or etching the through-hole 24 is performed as explained above (e.g. using a removable support layer), in particular by etching the through-hole 24 in the region of the hole 28a. In the same or a subsequent step, the cantilever spring portion 34 is provided by etching from the second substrate surface 12b the hole 35 next to the through-hole 34, in particular in the region of the hole 28b. In this way, the cantilever portion 34 is provided in between the through-hole 24 and the hole 35. If the etching of the hole 35 is performed in the same step as etching of the through-hole 24, no additional processing steps are required. Only a modification of the etch mask used is needed. Even though in the example of FIG. 13, the etching is performed from the second surface 12b (or backside) of the substrate 12 (or wafer), it will be understood that the etching can also be performed from the first surface 12a (or frontside) of the substrate 12 (or wafer), or a combination of both. For example, by also etching a cantilever spring-like structure from the first substrate surface 12a, much more complicated cantilever spring structures can be realized. The cantilever spring portion 34 is particularly useful if the electrical connection between the isolation-free end portion 18a and the electrical connection part 16 is performed by soldering (using a solder connection 32). In this case, the assembly step consists of only two phases, wherein first the electrical wire 18 is arranged or inserted in the through-hole, and second the end portion 18a of the wire is connected to the electrical connecting pad by immersing the device/arrangement 10 and the electrical wire in a solder bath. Thus, the device/arrangement 10 needs to be transported from the point where the wire 18 is inserted to the solder bath. In this case, the cantilever spring portion 34 can assist in keeping the device/arrangement 10 (e.g. silicon chip) attached to the electrical wire. The cantilever spring portion 34 acts as a mechanical clamp. Thus, there is no risk that the electrical wire 18 gets detached when the device/arrangement 10 is dipped into the solder bath.

Even though in the embodiment shown in FIG. 6 electrical connection between the isolation-free end portion 18a and the electrical connection part 16 is provided and particular useful using a solder connection 32, it will be understood that any other suitable electrical connection can be used, in particular any of the other electrical connections disclosed herein. Further, in the embodiment shown in FIG. 6, the isolating layer 28 comprises the thick portion 29 as explained with reference to FIG. 4. However, it will be understood that any other suitable isolating layer can be used.

In the above mentioned embodiments of FIGS. 1 to 6, only one through-hole 24 is illustrated in the drawing. However, it will be understood that for any of the above described embodiments a plurality of through-holes 24 can be provided in the substrate 12. A (single) electrical wire 18 or conductive core 20 is then arranged through each through-hole 24. In a corresponding method, providing in the substrate 12 the through-hole 24 then comprises a step of providing a plurality of through-holes 24 in the substrate 12, wherein an electrical wire 18 or conductive core 20 is arranged through each through-hole 24. For example, the electrical wire 18 can comprise a plurality (or strand) of conductive cores 20 and a (single) isolation 20 surrounding the plurality of conductive cores 20. This is also known as a "miniature flat cable". By providing each through-hole 24 extending through the whole thickness t of the substrate 12, the connection of a plurality (or strand) of such miniature electrical wires or conductive cores 20 to the electronic circuit arrangement 14 (e.g. silicon chip) can be reduced to one or two operations, which allows a significant reduction of cost. For example, the isolation 22 of the miniature flat cable can be stripped in one operation (e.g. by laser ablation). For example, in case of soldering, the wires or cores can all be soldered in one operation (e.g. by solder dipping).

The electronic circuit arrangement 10 disclosed herein is particularly useful in a sensor and/or actuator arrangement (e.g. electronic sensor chip). The sensor and/or actuator arrangement comprises the electrical circuit arrangement 10 disclosed herein, in particular according to any of the embodiments of FIG. 1 to FIG. 6, and at least one sensor and/or actuator 40. The electrical circuit 14 is configured to transmit electrical signals to the at least one actuator and/or receive electrical signals from the at least one sensor. The electrical wire 18 may for example electrically connect the at least one sensor and/or actuator 40 and the electrical circuit 14. In one example, the at least one sensor and/or actuator 40 is an optical camera. In another example, the at least one sensor and/or actuator 40 is an ultrasound transducer, in particular for ultrasound imaging. In a further example, the at least one sensor and/or actuator 40 is a temperature, pressure and/or flow sensor.

Figure 8:
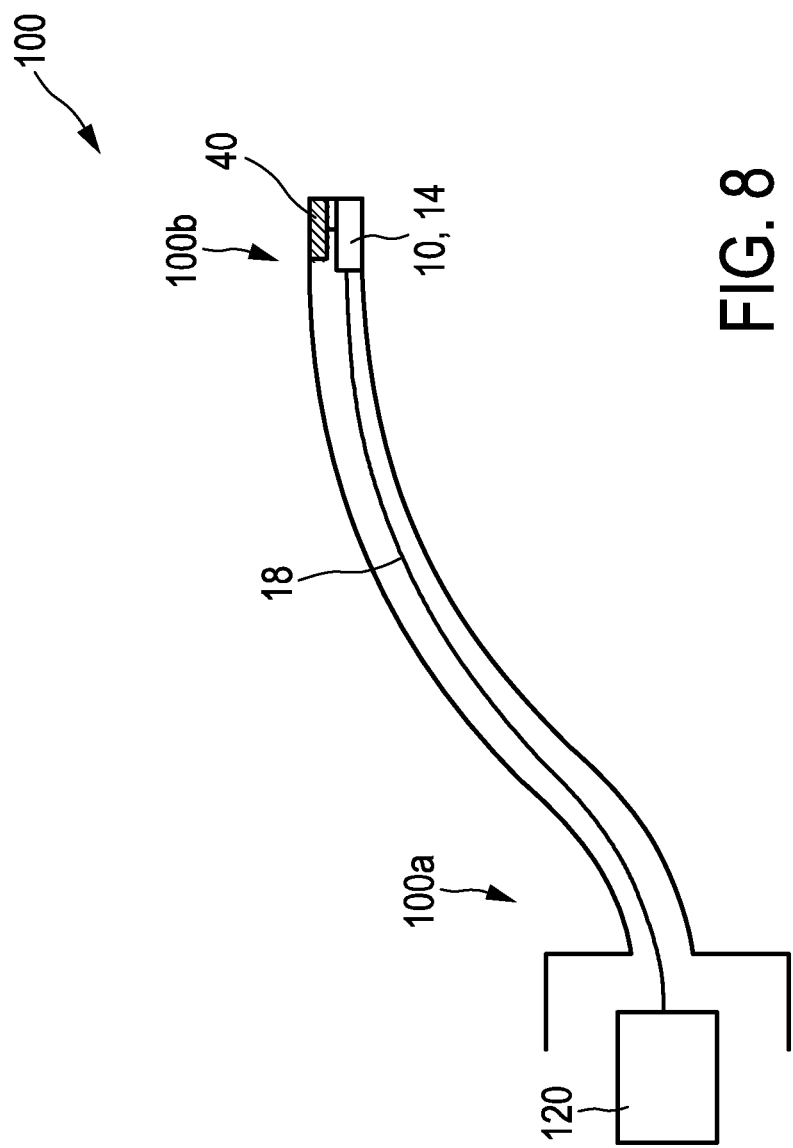
FIG. 8 shows a schematic diagram of a medical device according to an embodiment.

This sensor and/or actuator arrangement can for example be mounted or arranged at the distal end or tip of a medical instrument, in particular a minimal invasive medical instrument (e.g. a catheter or a catheter guide wire). FIG. 8 shows a schematic diagram of a medical device 100 according to an embodiment. The medical instrument 100, in particular a minimal invasive medical instrument, has a proximal end 100a and a distal end 100b. The medical instrument 100 comprises the sensor and/or actuator arrangement disclosed herein, wherein the sensor and/or actuator arrangement is arranged at the distal end 100b of the medical device 100. In the embodiment of FIG. 8, the electrical wire 18 leads from the distal end 100b of the medical device 100 to a signal readout and/or control device 120 at the proximal end 100a of the medical device 100. The signal readout and/or control device 120 can be configured to read out the electrical signals received from the sensor and/or actuator arrangement. Alternatively or cumulatively, the signal readout and/or control device 120 can be configured to control the operation of the sensor and/or actuator 40 by sending a control signal to the sensor and/or actuator arrangement. For example, in the case of treatment, the signal readout and/or control device 120 can be configured to control the operation of an ablation actuator (i.e. control an ablation process) or can control the operation a stimulation actuator (i.e. provide control signals for stimulation, e.g. of cells or nerves).

Even though the electrical circuit arrangement and the sensor and/or actuator arrangement has been described in connection with a medical instrument herein, it shall be understood that the electrical circuit arrangement or the sensor and/or actuator arrangement disclosed herein can also be used in connection with any other suitable device or instrument.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. An electronic circuit arrangement comprising:
    a substrate comprising a conductive or semi-conductive main portion and an isolating layer covering at least part of the main portion, the substrate having a first surface and a second surface,
    an electronic circuit,
    an electrical connection part for providing an electrical connection to the electronic circuit and being arranged on the first surface, and
    at least one electrical wire, the at least one electrical wire comprising a single conductive core and an isolation surrounding the conductive core, wherein an end portion of the at least one electrical wire is an isolation-free portion for allowing access to the conductive core, wherein the end portion of the at least one electrical wire is connected to the electrical connection part,
    wherein at least one through-hole extending from the first surface to the second surface is provided in the substrate, wherein the at least one through-hole comprises a first portion open to the first surface and having a first diameter and a second portion open to the second surface and having a second diameter bigger than the first diameter, wherein the first diameter is equal or bigger than a diameter of the conductive core and smaller than a diameter of the isolation, and wherein the at least one electrical wire is arranged through the at least one through-hole,
    wherein the isolating layer covers at least the sidewalls of the first portion of the at least one through-hole.

2. The electronic circuit arrangement of claim 1, wherein the at least one through-hole comprises a plurality of through-holes, wherein the at least one electrical wire or the conductive core is arranged through each of the plurality of through-holes.

3. The electronic circuit arrangement of claim 1, wherein the main portion is made of silicon.

4. The electronic circuit arrangement of claim 1, wherein the end portion of the at least one electrical wire is connected to the electrical connection part using a wedge bonding connection or a solder connection.

5. The electronic circuit arrangement of claim 1, wherein the isolating layer covers the first surface and comprises a thick portion surrounding the at least one through-hole, the thick portion having a thickness which is at least a length of the first portion of the at least one through-hole.

6. The electronic circuit arrangement of claim 1, wherein the electrical connection part comprises at least one cantilever spring contacting the end portion of the at least one electrical wire.

7. The electronic circuit arrangement of claim 1, wherein the substrate comprises at least one cantilever spring portion holding the at least one electrical wire in place.

8. A sensor and/or actuator arrangement comprising the electrical circuit arrangement of claim 1 and at least one sensor and/or actuator, wherein the electrical circuit is configured to transmit electrical signals to the at least one actuator and/or receive electrical signals from the at least one sensor.

9. The sensor and/or actuator arrangement of claim 8, wherein the at least one sensor and/or actuator is at least one device selected from the group comprising an optical camera, an ultrasound transducer, and a temperature, pressure and/or flow sensor.

10. A medical instrument, in particular a minimal invasive medical instrument, having a proximal end and a distal end and comprising the sensor and/or actuator arrangement of claim 8, wherein the sensor and/or actuator arrangement is arranged at the distal end of the medical device.

* * * * *